United States Patent [19]

Goudie

[11] 4,200,645
[45] Apr. 29, 1980

[54] PYRROLE DERIVATIVES

[75] Inventor: Alexander C. Goudie, Harlow, England

[73] Assignee: Beecham Group Limited, Great Britain

[21] Appl. No.: 903,194

[22] Filed: May 5, 1978

[30] Foreign Application Priority Data

May 10, 1977 [GB] United Kingdom ............... 19465/77
Jan. 28, 1978 [GB] United Kingdom ............... 03529/78

[51] Int. Cl.$^2$ .................... C07D 207/32; A61K 31/40
[52] U.S. Cl. ............................... 424/274; 260/326.35; 260/326.36; 260/326.47; 260/326.5 D; 260/326.5 SM; 260/326.5 J
[58] Field of Search ............... 260/326.5 J, 326.5 SM, 260/326.47, 326.5 D, 326.36, 326.35; 424/274

[56] References Cited

U.S. PATENT DOCUMENTS

| | | |
|---|---|---|
| 3,655,693 | 4/1972 | Shen et al. ...................... 260/326.5 J |
| 3,707,478 | 12/1972 | Carson ........................... 260/326.5 J |
| 3,721,680 | 3/1973 | Carson ........................... 260/326.5 J |
| 3,752,826 | 8/1973 | Carson ........................... 260/326.5 J |
| 3,803,169 | 4/1974 | Carson ........................... 360/326.5 J |
| 3,846,447 | 11/1974 | Carson ........................... 260/326.5 J |
| 3,952,012 | 4/1976 | Carson ........................... 260/326.47 |
| 3,998,844 | 12/1976 | Carson ........................... 260/326.5 J |
| 4,048,191 | 9/1977 | Carson ........................... 260/326.5 J |

OTHER PUBLICATIONS

Pesson et al., Chem. Abs., vol. 66:2431z, (1967).

*Primary Examiner*—Mary C. Lee
*Attorney, Agent, or Firm*—Jacobs & Jacobs

[57] ABSTRACT

The compounds of the formula:

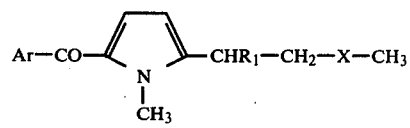

and pro-drugs therefor wherein $R_1$ is a hydrogen atom or a methyl group; Ar is a phenyl group or is a phenyl group substituted by one or two moieties selected from fluorine, chlorine, bromine, methyl, methoxyl or trifluoromethyl or is a thienyl group; and X is a CO or CHOH group have anti-inflammatory activity.

73 Claims, No Drawings

PYRROLE DERIVATIVES

The present invention relates to pyrrole derivatives, to a process for their preparation and to compositions containing them.

Tolmetin, a clinically used anti-inflammatory and analgesic agent of the formula (I):

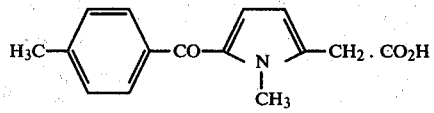

has been reported in J. Pharmacol. Exptl. Therap. 1973, 185, 127–138 to possess anti-inflammatory activity. Tolmetin and related compounds have also been described in British Patent Specification No: 1,195,628. It has been found that tolmetin causes gastric irritancy in test animals at doses not greatly exceeding the therapeutic dose. A group of anti-inflammatory and analgesic compounds has now been found which have reduced propensity to cause gastric irritancy. These compounds may be thus used in pharmaceutical compositions for the treatment of inflammatory or painful conditions such as rheumatism, arthritis or the like.

The present invention provides the compounds of the formula (II):

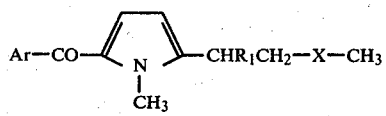

wherein $R_1$ is a hydrogen atom or methyl group; Ar is a phenyl group or a phenyl group substituted by one or two groups selected from fluorine, chlorine, bromine, methyl, methoxyl or trifluoromethyl or is a thienyl group; X is a CO or CHOH group; and pro-drugs thereof.

Suitably Ar is a phenyl or substituted phenyl group.

More suitably Ar is a phenyl or mono-substituted phenyl group.

Particularly apt groups Ar include the phenyl, methylphenyl, trifluoromethyl, chlorophenyl and the methoxyphenyl group.

A favoured group Ar is the phenyl group. A further favoured group Ar is the 4-methylphenyl. Another favoured group Ar is the 4-chlorophenyl group. Yet a further favoured group Ar is the 4-fluorophenyl group. Yet another favoured group Ar is the 4-methoxyphenyl group.

Other suitable values for Ar include di-halogenated phenyl such as di-chlorophenyl, for example 2,4-dichlorophenyl.

Suitably Ar is a thienyl group. A favoured group Ar is the 2-thienyl group. A further favoured group Ar is the 3-thienyl group.

Suitably $R_1$ in the preceding compounds represents a hydrogen atom.

Suitably $R_1$ in the preceeding compounds represents a methyl group.

Suitably X in the preceeding compounds is a CO group.

Suitably X in the preceeding compounds is a CHOH group.

When used herein the term 'pro-drug' means a compound metabolised in-vivo to or via a compound of the formula (II).

The pro-drugs will be derivatives of the group X, for example those wherein the 2-position side chain is the sub-formulae (a)–(d):

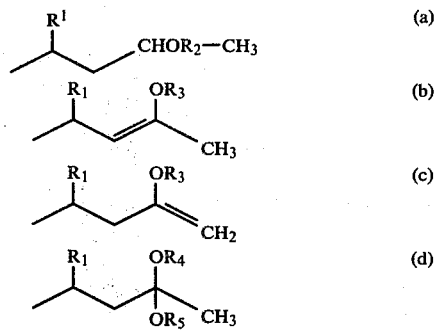

wherein $R_1$ is a hydrogen atom or a methyl group; $R_2$ is a group $CO.R_6$ wherein $R_6$ is the residue of a pharmaceutically acceptable carboxylic acid of up to 9 carbon atoms of the formula $R_6COOH$; $R_3$ is a $C_{1-4}$ alkyl group or a $CO.R_6$ group; $R_4$ is a methyl, ethyl or propyl group and $R_5$ is a methyl, ethyl or propyl group or $R_5$ is joined to $R_4$ so that they together represent a $CH_2CH_2$ or $CH_2CH_2CH_2$ group.

A favoured 2-position side chain in the preceeding compounds is the $CH_2.CH_2.CO.CH_3$ group.

Another favoured 2-position side chain in the preceeding compounds is the $CH_2.CH_2.CHOH.CH_3$ group.

Further favoured 2-position side chains are those of the formula $CH_2.CH_2.CH(O.CO.R_6)CH_3$ wherein $R_6$ is as defined in relation to sub-formula (a).

Apt values for $R_6$ include phenyl, alkyl of 1–4 carbon atoms, and alkyl of 1–4 carbon atoms substituted by phenyl, or one of the aforementioned groups substituted by a hydroxyl, acetoxyl, methoxyl, acetamido, optionally salted amino or alkylamino or optionally salted carboxyl group.

Favoured values for $R_6$ include the methyl, ethyl, n-propyl, iso-propyl, t-butyl, phenyl, benzyl, phenylethyl, acetoxymethyl, methoxymethyl, hydroxymethyl optionally salted aminoethyl, α-acetoxyphenyl, 4-methoxyphenyl, 3,4-dimethoxyphenyl and 3,4,5-trimethoxyphenyl groups.

Particularly suitable values for $R_6$ include the methyl, ethyl, benzyl, 2-methoxyphenyl, phenyl and 3,4,5-trimethoxyphenyl group.

A preferred group $R_6$ is the methyl group.

From the foregoing it will be realised a further favoured 2-position side chain is the $CH_2.CH_2.CH(O.CO.CH_3)CH_3$ group.

One group of favoured 2-position side chains is that of the formula $CH_2CH_2X^1CH_3$ where $X^1$ is a CO, CHOH or $CHOCOR_7$ group where $R_7$ is an alkyl group of 1–4 carbon atoms. Most suitably $R_7$ is a methyl group.

These compounds of the formula (II) wherein $R_1$ is a methyl group may be in the form of an isolated optical isomer or may be presented as a mixture of isomers, for example the R, S or RS form.

These compounds of the formula (II) wherein X is a CHOH or $CHOR_2$ group may be in the form of an isolated optical isomer or may be presented as a mixture of isomers, for example as the R, S or RS form.

Certain particularly effective compounds of this invention include those of the formula (IV):

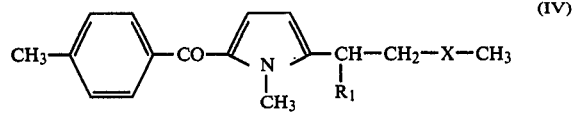

wherein $R_1$ is a hydrogen atom or methyl group and X is a CO, CHOH or CH.OCOCH$_3$ group.

In the compounds of formula (IV) $R_1$ is suitably a hydrogen atom. In the compounds of the formula (IV) $R_1$ is suitably a methyl group.

In the compounds of the formula (IV) X is suitably a CO group. In the compounds of the formula (IV) X is suitably a CHOH group. In the compounds of the formula (IV) X is suitably a CHOCOCH$_3$ group.

Certain other particularly effective compounds of this invention include those of the formula (V):

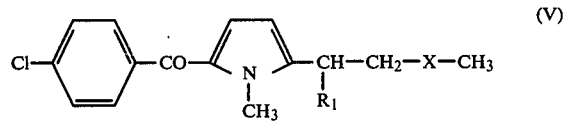

wherein $R_1$ is a hydrogen atom or a methyl group and X is a CO, CHOH or CH.O.CO.CH$_3$ group.

In the compounds of the formula (V) $R_1$ is suitably a hydrogen atom. In the compounds of the formula (V) $R_1$ is suitably a methyl group.

Suitably in the compounds of the formula (V) X is a CO group. Suitably in the compounds of the formula (V) X is a CHOH group. Suitably in the compounds of the formula (V) X is a CHOCOCH$_3$ group.

Certain further particularly effective compounds of this invention include those of the formula (VI):

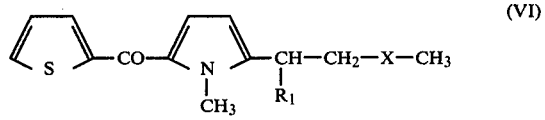

wherein $R_1$ is a hydrogen atom or a methyl group and X is a CO, CHOH or CHOCOCH$_3$ group.

In the compounds of the formula (VI) $R_1$ is suitably a hydrogen atom. In the compounds of the formula (VI) $R_1$ is suitably a methyl group.

In the compounds of the formula (VI) X is suitably a CO group. In the compounds of the formula (VI) X is suitably a CHOH group. In the compounds of the formula (VI), X is suitably a CHOCOCH$_3$ group.

Particularly suitable compounds of this invention include:

4-(1-methyl-5-p-toluoyl-2-pyrryl)butan-2-one;
2-acetoxy-4-(1-methyl-5-p-toluoyl(-2-pyrryl)butane;
4-(1-methyl-p-chlorobenzoyl-2-pyrryl)butan-2-one;
4-(1-methyl-p-chlorobenzoyl-2-pyrryl)butan-2-ol;
2-acetoxy-4-(1-methyl-5-p-chlorobenzoyl-2-pyrryl)-butane;
4-(1-methyl-5-thien-2'-oyl-2-pyrryl)butan-2-one;
4-(1-methyl-5-thien-2'-oyl-2-pyrryl)butan-2-ol;
2-acetoxy-4-(1-methyl-5-thien-2'-oyl-2-pyrryl)-butane.

4-(1-methyl-5-p-toluoyl-2-pyrryl)butan-2-ol.

In a further aspect this invention provides a pharmaceutical composition which comprises a compound of the formula (II) and a pharmaceutically acceptable carrier.

The compositions of this invention are useful in treating rheumatic and arthritic conditions because of their anti-inflammatory and analgesic properties. The compositions may be adapted for administration via the oral, rectal or injection routes but since the compositions of this invention do not excessively irritate the gastrointestinal tract it is preferred that they are adapted for oral administration.

The compositions of this invention may contain diluents, binders, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicylic acid or other anti-inflammatory analgesic agent.

Most suitably the composition of this invention will be in the form of a unit dose such as a tablet, capsule or reconstitutable powder in a sachet. Such unit doses will generally contain from 20 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 Kg adult will usually be in the range 200 to 4000 mg and more usually in the range 300 to 3000 mg for example 500 to 2000 mg. Alternatively the unit dose may contain from 2-20 mg of active agent and may be administered in multiples if desired to give the preceeding daily dose.

A favoured form of the composition of this invention is a hard gelatin capsule containing the active agent. The active agent may be in the form of a powder, granulate or the like and may advantageously be in intimate mixture with a lubricant such as magnesium stearate.

A further favoured form of the composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

The present invention also provides a method of treating inflammatory and/or painful conditions in mammals which comprises administering per day from 200 to 4000 mg of a compound of this invention and more usually from 300 to 3000 mg for example from 500 to 2000 mg of a compound of this invention.

Mammals which may be thus treated include humans and domestic animals such as dogs, cats or horses.

Most suitably the medicament will be administered orally as 2, 3, or 4 doses per day at the dose level previously indicated.

Often the condition treated will be arthritis.

The present invention provides a process for the preparation of a compound of the formula (I) or a prodrug thereof which process comprises the reaction of a compound of the formula (VII):

Ar.CO.Cl           (VII)

or its chemical equivalent wherein Ar is as defined in relation to formula (II), with a compound of the formula (IX):

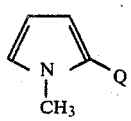
(IX)

wherein Q is a group of the sub-formulae (a)-(d) as hereinbefore defined or a group of the sub-formula (e):

—CHR₁—CH₂—CO—CH₃ (e)

wherein R₁ is a hydrogen atom or a methyl group; and thereafter if desired reducing the carbonyl present in a group of the subformula (e) to a CHOH group.

The present invention also provides a process for the preparation of the compounds of the formula (II) which process comprises the reaction of a compound of the formula (VII):

Ar.CO/Cl (VII)

or its chemical equivalent wherein Ar is as defined in relation to formula (II), with a compound of the formula (X):

(X)

wherein R₁ is as defined in relation to formula (II) and thereafter if desired reducing the carbonyl group X to a CHOH group X and/or thereafter converting the CO or CHOH group X to a pro-drug thereof.

The present invention also provides a process for the preparation of the pro-drugs of the compounds of the formula (II) which process comprises the reaction of a compound of the formula (VII) as hereinbefore defined or its chemical equivalent with a compound of the formula (XI):

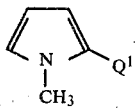
(XI)

wherein Q¹ is a group of the sub-formulae (a)-(d) as hereinbefore defined.

Suitable chemical equivalents of the compounds of the formula (VII) include the corresponding bromide, anhydride and the like for example the corresponding azide or mixed anhydride.

The reaction of the compounds of the formulae (VII) and (IX), (X) or (XI) takes place in an inert solvent or under conventional Friedel-Crafts acylation conditions, for example in an inert solvent and optionally in the presence of a Lewis acid such as aluminium chloride.

The acylation reaction is normally carried out at a non-extreme temperature for example from about 5° C. to 50° C. and more usually from about 10° C. to 30° C. if a Lewis acid is used. If no catalyst is used the acylation reaction is normally carried out at a higher temperature e.g. 100° C.

Suitable solvents for carrying out the acylation include tetrachloroethylene, chloroform, dichloromethane, dichloroethane, chlorobenzene or the like or benzene, toluene, nitrobenzene or the like.

The solvent system used for the process of this invention will be homogenous and will advantageously comprise an inert component and a tertiary amine. In general the inert component will predominate, for example it will comprise 60%–90% v/v of the total system and more usually from 80% to 92% v/v. Toluene and tetrachloroethylene are favoured inert solvents. Suitable tertiary amines include conventional weak tertiary amines such as pyridine and the like.

When the solvent system employed contains a tertiary amine it is frequently advantageous not to employ a Lewis acid catalyst as acceptable yields are obtained in the absence of said catalyst. This form of the reaction may be performed at a low, ambient or elevated temperature but in general it is preferred to use a somewhat elevated temperature to ensure that the reaction is over in a reasonably short period. Thus, for example, a temperature of 40°–140° C. is generally suitable, for example 80°–120° C.

The product produced by acylation in the presence of a Lewis acid may be isolated in conventional manner, for example by diluting with an aqueous acid, extracting into an organic solvent, washing and drying the organic phase and thereafter evaporating the solvent. The resulting diketone may then be purified by chromatography and/or recrystallisation.

The product produced by acylation in the absence of a Lewis acid may often be obtained simply by the evaporation of the solvents. If the resulting product is required in a purer form it may normally be further purified by chromatography in conventional manner.

The diketones of the formula (II) may be converted to the corresponding compounds wherein X is a CHOH by careful reduction with a complex hydride such as sodium borohydride. The resulting compound may be separated by conventional methods of column chromatography from any contaminant resulting from reduction of the aromatic ketone.

The compounds wherein X is a CHOH group may be acylated in conventional manner, for example, by reaction with the acid R₂CO₂H in the presence of a condensation promoting agent such as dicyclohexylcarbodiimide in an aprotic solvent such as dichloromethane or tetrahydrofuran or by reaction with an acyl halide in the presence of an acid acceptor such as pyridine.

The conventional pro-drugs of the compounds of the formula (II) may be prepared from the compounds of the formula (II) in conventional manner.

Thus, for example, those compounds containing a side chain of the sub-formula (a) may be prepared by the acylation of a corresponding compound containing a side chain of the sub-formula (e):

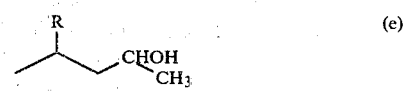
(e)

Suitable methods of acylation include those described in Belgian Pat. No: 854,429.

Also for example, those compounds containing a side chain of the sub-formulae (b), (c) or (d) may be prepared by the enol acylation or enol etherification of a corresponding compound containing a side chain of the subformula (f):

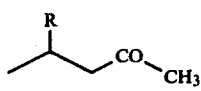

Suitable methods of enol acylation or enol etherification include those described in West German Application P2647966.3.

DESCRIPTION 1

4-(1-Methyl-2-pyrryl)-butan-2-one

A mixture of 4-(1-Methyl-2-pyrryl)-but-3-en-2-one (2.98 g) and 10% palladium on charcoal (0.2 g) was hydrogenated in ethyl acetate (50 ml) at room temperature and atmospheric pressure. The catalyst was removed by filtration the solvent evaporated, and the resulting oil left overnight to solidify in a refrigerator. The long, colourless needles which formed were washed with cold 60°–80° petrol to give 4-(1-Methyl-2-pyrryl)-butan-2-one (2.46 g).

EXAMPLE 1

4-(1-Methyl-5-p-toluoyl-2-pyrryl)butan-2-one

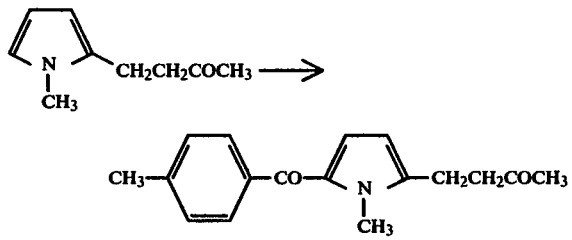

To a solution of 4-(1-Methyl-2-pyrryl)-butan-2-one (2.46 g) in dichloroethane (10 ml) at room temperature was added over 40 minutes a solution of dichloroethane (10 ml) containing aluminium chloride (2.17 g: 0.016 mole) and p-toluoyl chloride (2.52 g: 0.016 mole). After a further 20 minutes the mixture was treated with dilute hydrochloric acid (5 N, 10 ml) and extracted with dichloromethane (50 ml). The organic layer was washed with water (20 ml), aqueous unsymmetrical-dimethylethylenediamine (20% 20 ml), dilute hydrochloric acid (5 N, 10 ml) and extracted with dichloromethane (50 ml). The organic layer was washed with water (20 ml), aqueous unsymmetrical-dimethylethylenediamine (20% 20 ml), dilute hydrochloric acid (1 N. 20 ml) and finally brine (20 ml). After drying (Na₂SO₄) the mixture was concentrated to give a dark oil which was then chromatographed on alumina (150 g) using benzene as eluant. Recrystallisation of the solid fraction from 60°–80° petrol gave pure 4-(1-methyl-5-p-toluoyl-2-pyrryl)-butan-2-one, m.p. 103°–4°.

N.m.r. (CDCl₃) δ=7.65 (2H, d, J=8 Hz), 7.17 (2H, d, J=8 Hz), 6.6 (1H, d, J=4 Hz), 5.87 (1H, d, J=4 Hz), 3.92 (3H, s), 3.0–2.7 (4H, m), 2.38 (3H, s), 2.17 (3H, s).

EXAMPLE 2

4-(1-Methyl-5-p-toluoyl-2-pyrryl)butan-2-one

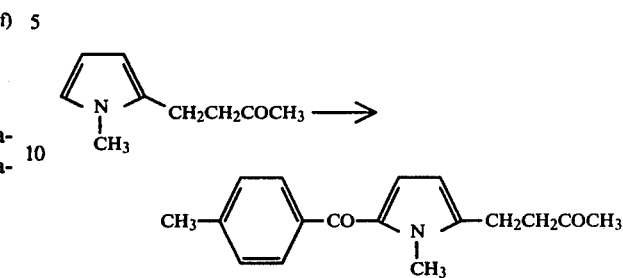

4-(1-Methyl-2-pyrryl)-butan-2-one (15 g) and p-toloyl chloride (37.5 ml) were dissolved in toluene (200 ml) and pyridine (30 ml). The mixture was heated under reflux for 7 hours. The resulting mixture was filtered and the filtrate evaporated (50° C. 15 mm/Hg) to leave an oil. The oil was extracted into hot 60°–80° C. petrol (4×250 ml) and the solution cooled (−30° C.) causing a solid to precipitate. This solid was purified by column chromatography (detection by t.l.c. using u.v.) to yield after evaporation of the solvent the desired 4-(1-methyl-5-p-toluoyl-2-pyrryl)-butan-2-one (40% yield) as a white solid, m.p. 103°–104° C.

N.m.r.—as described in Example 1. (The chromatographic system employed 300 g silica eluting with ethyl acetate/60°–80° petrol mixtures. The initial eluting solvent contained 10% ethyl acetate and brought through the benzophenone impurity. Increasing the concentration of the ethyl acetate to 20% then brought through the desired product).

EXAMPLE 3

4-(1-Methyl-5-p-chlorobenzoyl-2-pyrryl)butan-2-one

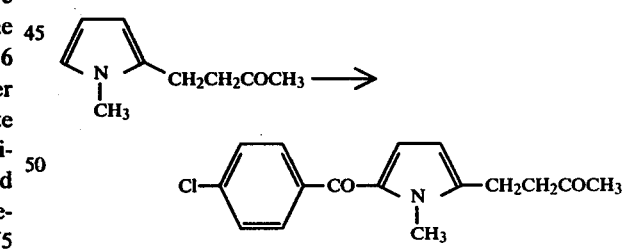

The title compound was prepared by the process as described in Example 2 except that p-chlorobenzoyl chloride was used as acylating agent and tetrachloroethylene as solvent. The crude product was purified by passage through alumina using methylene chloride as solvent, followed by recrystallisation from carbon tetrachloride to give pure 4-(1-methyl-5-p-chlorobenzoyl-2-pyrryl)-butan-2-one as colourless needles, m.p. 108°–109° C.

N.m.r. (CDCl₃) δ=7.7 (2H, d, J=9 Hz), 7.35 (2H, d, J=9 Hz), 6.53 (1H, d, J=4 Hz), 5.85 (1H, d, J=4 Hz), 3.93 (3H, s), 3.0–2.7 (4H, m), 2.15 (3H, s).

EXAMPLE 4

4-(1-Methyl-5-thien-2'-oyl-2-pyrryl)butan-2-one

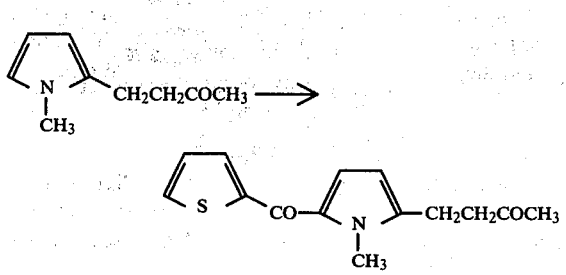

The title compound was prepared by the process described in Example 3 except that thien-2-oyl chloride was used as acylating agent. Recrystallisation from diethyl ether gave pure 4-(1-methyl-5-thien-2'-oyl-2-pyrryl)butan-2-one as rhombic crystals, m.p. 78°–79° C.

N.m.r. (CDCl$_3$) δ=8.1–6.9 (4H, m), 6.92 (1H, d, J=4 Hz), 3.87 (3H, s), 3.0–2.7 (4H, m), 2.19 (3H, s).

EXAMPLE 5

4-(1-Methyl-5-p-toluoyl-2-pyrryl)butan-2-ol

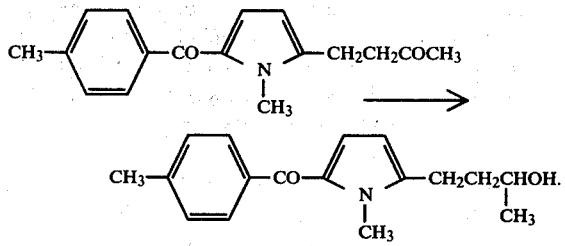

A mixture of 4-(1-methyl-5-p-toluoyl-2-pyrryl)-butan-2-one (2.35 g), sodium borohydride (0.4 g) and ethanol (350 ml) was stirred for 1 hour at room temperature before being treated with a saturated, aqueous solution of ammonium chloride (20 ml). This mixture was concentrated and then partitioned between water (50 ml) and methylene chloride (100 ml). The aqueous layer was extracted with methylene chloride (3×50 ml) and the combined organic layers were then washed with water (50 ml), dried (Na$_2$SO$_4$) and concentrated to afford somewhat crude 4-(1-methyl-5-p-toluoyl-2-pyrryl)butan-2-ol as a pale purple oil (2.06 g).

EXAMPLE 6

2-Acetoxy-4-(1-methyl-5-p-toluoyl-2-pyrryl)butane

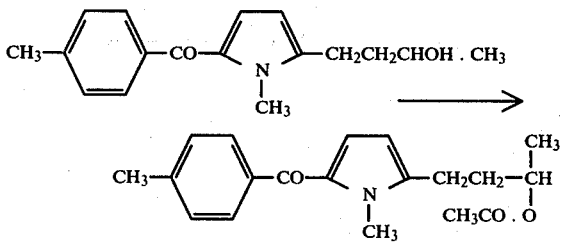

The product of Example 5 was taken up in toluene (100 ml) containing pyridine (4 ml), treated dropwise at 5° C. with acetyl chloride (2 ml) and then stirred at room temperature for 1 hour. The resulting mixture was added to cold water (100 ml) and extracted with diethyl ether (3×100 ml). The combined organic layers were washed with 1 N HCl (50 ml) and water (2×50 ml) and dried (Na$_2$SO$_4$) and concentrated to give a pale purple oil which slowly solidified on standing. Recrystallisation of this solid from diethyl ether gave pure 2-acetoxy-4-(1-methyl-5-p-toluoyl-2-pyrryl)butane as colourless needles, m.p. 88°–89°. N.m.r. (CDCl$_3$) δ=7.65 (2H, d, J=8 Hz), 7.2 (2 H, d, J=8 Hz), 6.64 (1H, d, J=4 Hz), 5.94 (1H, d, J=4 Hz), 4.97 (1H, q, J=6 Hz), 3.91 (3H, s), 2.9–1.7 (4H, m), 2.34 (3H, s), 2.03 (3H, s), 1.27 (3H, d, J=6 Hz).

EXAMPLE 7

2-Methyl-2-[2-(1-methyl-5-p-toluoyl-2-pyrryl)ethyl]-1,3-dioxolane

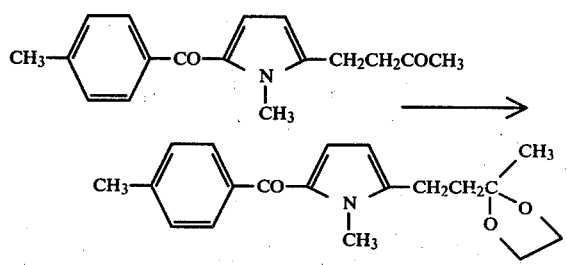

A mixture of 4-(1-Methyl-5-p-toluoyl-2-pyrryl)butan-2-one (1.0 g), ethylene glycol (6 ml), p-toluene-sulphonic acid (40 mg) and benzene (100 ml) was refluxed for 5 hours with constant separation of H$_2$O by means of a Dean-Stark trap. The mixture was cooled to room temperature, basified with 1 N sodium bicarbonate solution (20 ml) and extracted with chloroform (3×50 ml). The organic layer was washed with H$_2$O (2×50 ml), dried (Na$_2$SO$_4$) and concentrated to give a purple oil. This was chromatographed on alumina using ether as eluant to give pure 2-methyl-2-[2-(1-methyl-5-p-toluoyl-2-pyrryl)ethyl]1,3-dioxaolane as a colourless oil.

N.m.r. (CDCl$_3$), δ=7.69 (2H, d, J=8 Hz), 7.20 (2H, d, J=8 Hz), 6.64 (1H. d, J=4 Hz), 5.95 (1H, d, J=4 Hz), 3.99 (4H, s), 3.95 (3H, s), 3.0–1.8 (4H, m), 2.40 (3H, s), 1.39 (3H, s).

EXAMPLE 8

Compositions (a) Tablets of the following composition may be prepared:

| | |
|---|---|
| 4-(1-Methyl-5-p-toluoyl-2-pyrryl)butan-2-one | 25 mg |
| Microcrystalline cellulose | 123 mg |
| Magnesium Stearate | 2 mg |

(b) Hard gelatin capsules may be prepared containing the following:

| | |
|---|---|
| 4-(1-Methyl-5-p-toluoyl-2-pyrryl)butan-2-one | 50 mg |
| Lactose | 75 mg |
| Sodium lauryl sulphate | 5 mg |

EXAMPLE 9

Compositions (a) Tablets of the following composition may be prepared:

| | |
|---|---|
| 4-(1-Methyl-5-p-chlorobenzoyl-2-pyrryl)butan-2-one | 25 mg |
| Microcrystalline cellulose | 123 mg |
| Magnesium Stearate | 2 mg |

(b) Hard gelatin capsules may be prepared containing the following:

| | |
|---|---|
| 4-(1-Methyl-5-thien-2'-oyl-2-pyrryl)butan-2-one | 50 mg |
| Lactose | 75 mg |
| Sodium lauryl sulphate | 5 mg |

(c) Hard gelatin capsules may be prepared containing the following:

| | |
|---|---|
| 4-(1-Methyl-5-p-chlorobenzoyl-2-pyrryl)butan-2-one | 100 mg |
| Lactose | 25 mg |
| Sodium lauryl sulphate | 5 mg |

Demonstration 1 a. When tested on a conventional phenylquinone induced writhing test for analgesic activity, the compound of Example 1 and tolmetin produced the following $ED_{50}$ values when administered orally to mice:

| COMPOUND | $ED_{50}$ (mg/kg) | |
|---|---|---|
| | Test A | Test B |
| Comp. Example 1 | 6.7 | 5.3 |
| Tolmetin | 4.3 | 2.3 |

These results indicate that the compound of Example 1 is about half as potent as tolmetin as an analgesic agent.

b. Groups of 10 rats were starved overnight and then dosed orally with the test compound suspended in 0.7% methylcellulose. After a 4 hour contact time the animals were killed and the stomachs removed, inflated with 0.9% saline, cut open after 30 minutes and examined for erosions. The following results, expressed as the number of animals in each group showing damage, were obtained:

| | Dose (mg/kg) | No. of Animals Showing Erosions |
|---|---|---|
| Tolmetin | 90 | 10 |
| | 30 | 6 |
| | 10 | 2 |
| Compound of Example 1 | 270 | 1 |
| | 90 | 1 |
| | 30 | 0 |

This test indicates that tolmetin is probably at least 10 times as gastric irritant as the compound of Example 1.

c. When tested on a conventional carrageenin induced oedema test for anti-inflammatory activity, the compound of Example 1 was classed as active at 10 mg/kg per oral in rats (as compared to about 5 mg/kg for tolmetin).

d. No drug-induced lethalities have been observed with the compound of Example 1 during tested in rats at dosages up to 100 mg/kg per day for 6 days. The compound did not reduce body weight increase at this dose nor did it increase thymus weight.

DEMONSTRATION 2

When tested on a conventional cotton pellet induced granuloma test the results shown hereafter were obtained. In these tests hydrocortisone (HC) was used as a positive control.

| | Compound | Dose | Inhibition |
|---|---|---|---|
| a. | Comp. Example 3 | 10mg/kg | 42% |
| | HC | 10mg/kg | 43% |
| b. | Comp. Example 4 | 10mg/kg | 24% |
| | HC | 10mg/kg | 43% |
| c. | Comp. Example 6 | 50mg/kg | 34% |
| | HC | 10mg/kg | 43% |
| d. | Comp. Example 7 | 50mg/kg | 43% |
| | HC | 10mg/kg | 43% |

The compounds of Examples 3, 4, 6 and 7 were not found to exhibit any overt toxic effects during testing, for example no drug-induced lethalities were observed, no reduction in body weight gain was observed and no change in thymus weight was observed.

What we claim is:

1. A compound of the formula:

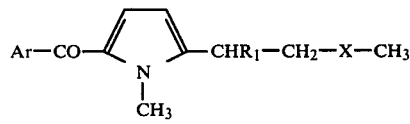

wherein
$R_1$ is hydrogen or methyl;
Ar is (a) phenyl unsubstituted or substituted by one or two members selected from the group consisting of fluoro, chloro, methyl, methoxy and trifluoromethyl; or (b) thienyl; and
X is CO or CHOH;
or a pro-drug therefore selected from the group consisting of a compound of the formula

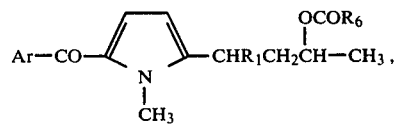

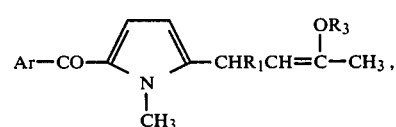

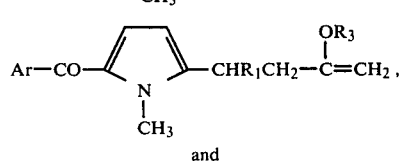

and

-continued

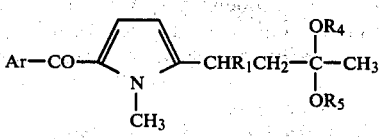

wherein

Ar and $R_1$ are as defined above, $R_6$ is a member selected from the group consisting of phenyl, alkyl of 1 to 4 carbon atoms, and phenylalkyl of 1 to 4 carbon atoms in the alkyl group, said member being unsubstituted or substituted with hydroxy, acetoxy, methoxy, acetamido, amino, alkylamino or carboxy, $R_3$ is alkyl of 1 to 4 carbon atoms or $COR_6$ wherein $R_6$ is as herein defined, and $R_4$ and $R_5$ when taken independently are each methyl, ethyl or propyl or when taken together are ethylene or trimethylene.

2. A compound according to claim 1 wherein Ar is phenyl, unsubstituted or substituted.

3. A compound according to claim 1 wherein Ar is phenyl, unsubstituted or mono-substituted.

4. A compound according to claim 1 wherein Ar is phenyl, methylphenyl, fluorophenyl, chlorophenyl, or methoxyphenyl.

5. A compound according to claim 1 wherein Ar is dichlorophenyl.

6. A compound according to claim 1 wherein Ar is a thienyl group.

7. A compound according to any of claim 1 wherein Ar is phenyl.

8. A compound according to claim 1 wherein Ar is methylphenyl.

9. A compound according to claim 1 wherein Ar is methoxyphenyl.

10. A compound according to claim 1 wherein Ar is chlorophenyl.

11. A compound according to claim 1 wherein Ar is fluorophenyl.

12. A compound according to claim 6 wherein Ar is 2-thienyl.

13. A compound according to claim 6 wherein Ar is 3-thienyl.

14. A compound according to claim 8 wherein Ar is 4-methylphenyl.

15. A compound according to claim 9 wherein Ar is 4-methoxyphenyl.

16. A compound according to claim 10 wherein Ar is 4-chlorophenyl.

17. A compound according to claim 11 wherein Ar is 4-fluorophenyl.

18. A compound according to claim 1 wherein $R_1$ is hydrogen.

19. A compound according to claim 1 wherein $R_1$ is methyl.

20. A compound according to claim 1 wherein X is CO.

21. A compound according to claim 1 wherein X is CHOH.

22. A compound according to claim 1 which is a pro-drug selected from the group consisting of a compound of the formula.

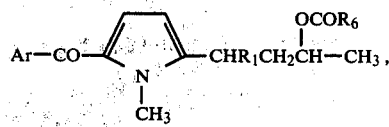

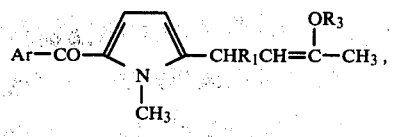

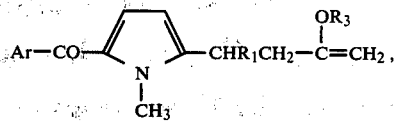

and

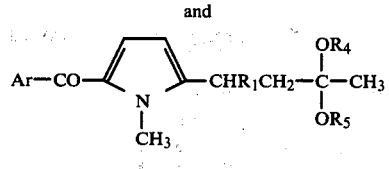

wherein

Ar and $R_1$ are as defined therein, $R_6$ is a member selected from the group consisting of phenyl, alkyl of 1 to 4 carbon atoms, and phenylalkyl of 1 to 4 carbon atoms, and phenylalkyl of 1 to 4 carbon atoms in the alkyl group, said member being unsubstituted or substituted with hydroxy, acetoxy, methoxy, acetamido, amino, alkylamino or carboxy, $R_3$ is alkyl of 1 to 4 carbon atoms or $COR_6$ wherein $R_6$ is as herein defined, and $R_4$ and $R_5$ when taken independently are each methyl, ethyl or propyl or when taken together are ethylene or trimethylene.

23. A compound according to claim 1 wherein $R_1$ is hydrogen and X is CO.

24. A compound according to claim 1 wherein $R_1$ is hydrogen and X is CHOH.

25. A compound according to claim 22 wherein said compound is of the formula

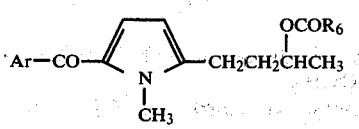

wherein $R_6$ and Ar are as therein defined.

26. A compound according to claim 25 wherein $R_6$ is methyl, ethyl, n-propyl, iso-propyl, t-butyl, phenyl, benzyl, phenylethyl, acetoxymethyl, methoxymethyl, hydroxymethyl optionally salted aminoethyl, α-acetoxyphenyl, 4-methoxyphenyl, 3,4-dimethoxyphenyl or 3,4,5-trimethoxyphenyl.

27. A compound according to claim 26 wherein $R_6$ is methyl, ethyl, benzyl, 2-methoxyphenyl, phenyl or 3,4,5-trimethoxyphenyl.

28. A compound according to claim 27 wherein $R_6$ is methyl.

29. A compound according to claim 25 wherein $R_6$ is alkyl of 1 to 4 carbon atoms.

30. A compound of the formula:

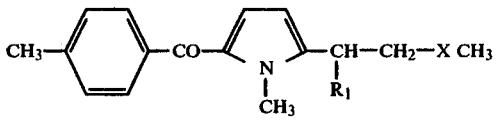

wherein R₁ is hydrogen or methyl and X is CO, CHOH or CHOCOCH₃.

31. A compound according to claim 30 wherein R₁ is hydrogen.

32. A compound according to claim 30 wherein R₁ is methyl.

33. A compound according to claim 30 wherein X is CO.

34. A compound according to claim 30 wherein X is CHOH.

35. A compound according to claim 30 wherein X is CHOCOCH₃.

36. A compound of the formula:

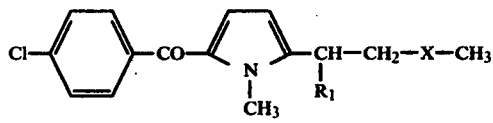

wherein R₁ is hydrogen or methyl and X is CO, CHOH or CHOCOCH₃.

37. A compound according to claim 36 wherein R₁ is hydrogen.

38. A compound according to claim 36 wherein R₁ is methyl.

39. A compound according to claim 36 wherein X is CO.

40. A compound according to claim 36 wherein X is CHOH.

41. A compound according to claim 36 wherein X is CHOCOCH₃.

42. A compound of the formula:

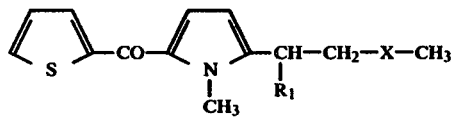

wherein R₁ is hydrogen or methyl and X is CO, CHOH or CHOCOCH₃.

43. A compound according to claim 42 wherein R₁ is hydrogen.

44. A compound according to claim 42 wherein R₁ is methyl.

45. A compound according to claim 42 wherein X is CO.

46. A compound according to claim 42 wherein X is CHOH.

47. A compound according to claim 42 wherein X is CHOCOCH₃.

48. The compound according to claim 30 which is 4-(1-methyl-5-p-toluoyl-2-pyrryl)butan-2-one.

49. The compound according to claim 30 which is 4-(1-methyl-5-p-toluoyl-2-pyrryl)butan-2-ol.

50. The compound according to claim 30 which is 2-acetoxy-4-(1-methyl-5-p-toluoyl-2-pyrryl)butane.

51. The compound according to claims 36 which is 4-(1-methyl-5-p-chlorobenzoyl-2-pyrryl)butan-2-one.

52. The compound according to claim 36 which is 4-(1-methyl-5-p-chlorobenzoyl-2-pyrryl)butan-2-ol.

53. The compound according to claim 36 which is 2-acetoxy-4-(1-methyl-5-p-chlorobenzoyl-2-pyrryl)butane.

54. The compound according to claim 42 which is 4-(1-methyl-5-thien-2'-oyl-2-pyrryl)butan-2-one.

55. The compound according to claim 42 which is 4-(1-methyl-5-thien-2'-oyl-2-pyrryl)butan-2-ol.

56. The compound according to claim 42 which is 2-acetoxy-4-(1-methyl-5-thien-2'-oyl-2-pyrryl)butane.

57. A compound according to claim 1 wherein Ar is dihalophenyl.

58. A compound according to claim 57 wherein Ar is dichlorophenyl.

59. A compound according to claim 58 wherein Ar is 2,4-dichlorophenyl.

60. An antiinflammatory and analgesic pharmaceutical composition comprising an effective amount of a compound according to claim 1 in combination with a pharmaceutically acceptable carrier.

61. A composition according to claim 60 adapted for oral administration.

62. A composition according to claim 60 in unit dosage form and containing from 20 to 1000 mg of said compound.

63. A composition according to claim 62 containing from 30 to 500 mg of said compound.

64. A composition according to claim 63 containing from 50 to 250 mg of said compound.

65. A method of effecting an antiinflammatory and analgesic response in domestic mammals and humans which comprises the administration thereto per day of from 200 to 4000 mg of a compound according to claim 1.

66. A method according to claim 65 wherein from 300 to 3000 mg of said compound are administered per day.

67. A method according to claim 66 wherein from 500 to 2000 mg of said compound are administered per day.

68. An antiinflammatory and analgesic pharmaceutical composition comprising an effective amount of a compound according to claim 30 in combination with a pharmaceutically acceptable carrier.

69. An antiinflammatory and analgesic pharmaceutical composition comprising an effective amount of a compound according to claim 36 in combination with a pharmaceutically acceptable carrier.

70. An antiinflammatory and analgesic pharmaceutical composition comprising an effective amount of a compound according to claim 42 in combination with a pharmaceutically acceptable carrier.

71. A method of effecting an antiinflammatory and analgesic response in domestic mammals and humans which comprises the administration thereto per day of from 200 to 4000 mg of a compound according to claim 30.

72. A method of effecting an antiinflammatory and analgesic response in domestic mammals and humans which comprises the administration thereto per day of from 200 to 4000 mg of a compound according to claim 36.

73. A method of effecting an antiinflammatory and analgesic response in domestic mammals and humans which comprises the administration thereto per day of from 200 to 4000 mg of a compound according to claim 42.

* * * * *